US011609215B2

United States Patent
Matsuyama et al.

(10) Patent No.: US 11,609,215 B2
(45) Date of Patent: Mar. 21, 2023

(54) GAS SENSOR

(71) Applicant: NGK SPARK PLUG CO., LTD., Nagoya (JP)

(72) Inventors: Daisuke Matsuyama, Nagoya (JP); Masahiro Asai, Nagoya (JP); Masashi Nomura, Nagoya (JP); Yuto Inose, Nagoya (JP); Takehiro Oba, Nagoya (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 0 days.

(21) Appl. No.: 17/075,110

(22) Filed: Oct. 20, 2020

(65) Prior Publication Data
US 2021/0132016 A1    May 6, 2021

(30) Foreign Application Priority Data

Nov. 5, 2019  (JP) .............................. JP2019-200447
Jun. 19, 2020  (JP) .............................. JP2020-106324

(51) Int. Cl.
*G01N 33/00*  (2006.01)

(52) U.S. Cl.
CPC ................................ *G01N 33/0016* (2013.01)

(58) Field of Classification Search
CPC ........... G01N 33/0016; G01N 33/0009; G01N 27/4077; G01N 27/4062; G01N 27/409; C04B 35/00

See application file for complete search history.

(56) References Cited

U.S. PATENT DOCUMENTS 4,668,477 A  *  5/1987  Nishio ............... G01N 27/4077
                                                    73/31.05
2009/0100907 A1*  4/2009  Mizutani ............ G01N 27/4077
                                                    73/31.05
(Continued)

FOREIGN PATENT DOCUMENTS

JP            63115751 U      7/1988
JP         2004245663 A       9/2004
JP         2016-095223 A      5/2016

OTHER PUBLICATIONS

Notice of Reasons for Refusal dated Jan. 10, 2023 for the corresponding Japanese Patent Application No. 2020-106324 (8 pages including English translation).

*Primary Examiner* — Francis C Gray
(74) *Attorney, Agent, or Firm* — Leason Ellis LLP; Melvin C. Garner; Mitsuhiro Haraguchi

(57) ABSTRACT

A gas sensor includes a gas sensor element for detecting the concentration of a specific gas in a gas under measurement, a tubular housing having an opening, a sealing member closing the opening, and a heat dissipating member having a rear end located at the same position or forward of the rear end of the housing. The heat dissipating member reduces heat transferred from the forward end side of the gas sensor to the sealing member and includes a connection portion connected to the housing, and a main portion extending rearward from the connection portion such that a gap is formed between the main portion and the housing. The main portion has heat dissipating openings for establishing communication between the gap and a space on the outer circumferential side of the heat dissipating member. The heat dissipating openings are formed on the rear end side of the main portion.

9 Claims, 10 Drawing Sheets

(56) References Cited

U.S. PATENT DOCUMENTS

| | | | | |
|---|---|---|---|---|
| 2014/0299469 A1* | 10/2014 | Oba | ................... | G01N 27/407 |
| | | | | 204/412 |
| 2014/0338424 A1* | 11/2014 | Kume | ................ | G01M 15/102 |
| | | | | 73/31.05 |
| 2018/0217088 A1* | 8/2018 | Tahira | ............... | G01N 27/4077 |

\* cited by examiner

GAS SENSOR

This application claims the benefit of priority to Japanese Patent Applications No. 2019-200447 filed on Nov. 5, 2019, and No. 2020-106324 filed on Jun. 19, 2020, the contents of which are incorporated herein by reference in their entireties.

FIELD OF THE INVENTION

The present disclosure relates to a gas sensor.

BACKGROUND OF THE INVENTION

Japanese Patent Application Laid-Open (kokai) No. 2016-95223 discloses a known gas sensor for detecting the concentration of a specific component (such as oxygen or NOx) in exhaust gas from an internal combustion engine. This gas sensor includes a gas sensor element extending in the axial direction, a metallic shell which surrounds the outer circumference of the gas sensor element and holds the gas sensor element and which is attached to an exhaust pipe, an outer tube fixed to the rear end of the metallic shell and extending rearward in the axial direction, and a grommet which is disposed inside a rear end portion of the outer tube and is in contact with the outer tube. Since a tubular protecting member is attached to the outer circumference of the outer tube, the outer tube can be protected from flying stones, etc., which would otherwise hit against the outer tube.

The protecting member includes a connection portion connected to the outer circumference of the outer tube by, for example, laser welding, and a main portion extending rearward from the connection portion and spaced apart from the outer circumference of the outer tube. Heat of the gas sensor transfers from the outer tube to the connection portion and is dissipated from the connection portion to the main portion, so that the amount of heat transferred from the outer tube to the grommet can be reduced.

Problem to be Solved by the Invention

However, in the above-described gas sensor, heat tends to accumulate between the outer tube and the protecting member. In order to avoid the accumulation of heat, a plurality of openings are provided in the protecting member so as to introduce the outside air into the interior of the protecting member. Since each of the openings also plays a role in draining water from inside the protecting member, the positions of the openings are located below the grommet.

SUMMARY OF THE INVENTION

Means for Solving the Problems

A gas sensor of the present disclosure is a gas sensor extending in an axial direction from a forward end toward a rear end and comprising: a gas sensor element that is configured to detect the concentration of a specific gas in a gas under measurement; a tubular housing surrounding the gas sensor element and having an opening at a rear end of the housing; a sealing member closing the opening; and a tubular heat dissipating member surrounding the housing and having a rear end located at the same position as the rear end of the housing or located forward of the rear end of the housing, the heat dissipating member reducing the amount of heat transferred from the forward end side of the gas sensor to the sealing member through the housing. The heat dissipating member includes a connection portion connected to the housing on the forward end side of the sealing member, and a main portion extending rearward from the connection portion such that a gap is formed between the main portion and the housing. The main portion has a heat dissipating opening that is configured to establish communication between the gap and a space on the outer circumferential side of the heat dissipating member, the heat dissipating opening being located rearward of the center of the main portion in the axial direction.

Effect of the Invention

According to the present disclosure, it is possible to avoid the influence of heat on a rear end portion of the gas sensor, for example, the influence of heat on the sealing member.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Figure 1:
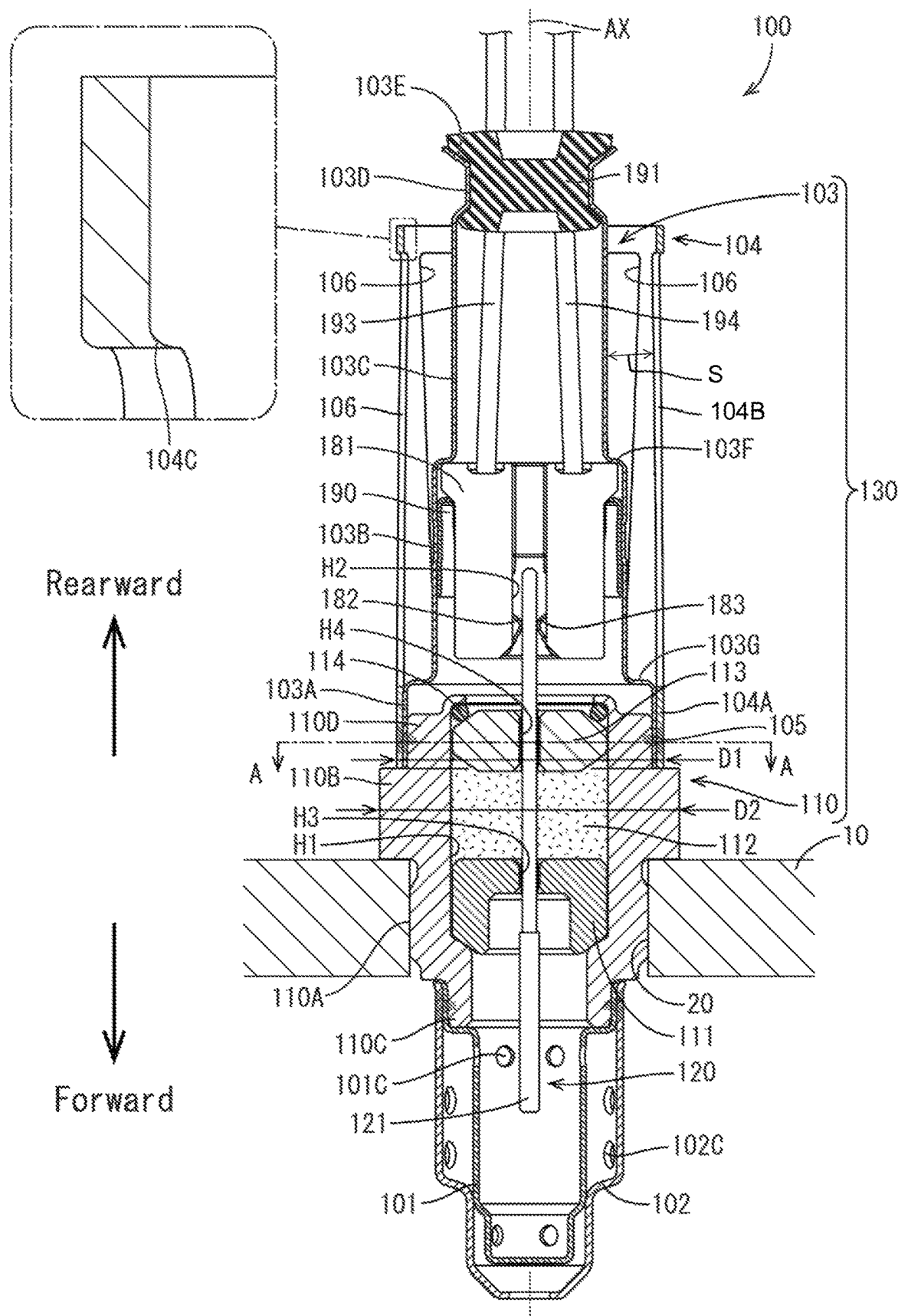
FIG. 1 is a cross-sectional view showing an internal structure of a gas sensor with a partially enlarged cross-sectional view showing a burr according to a first embodiment of the present disclosure.

[Descriptions of Embodiments of the Present Disclosure]

First, embodiments of the present disclosure will be listed and described.

(1) A gas sensor of the present disclosure is a gas sensor extending in an axial direction from a forward end toward a rear end and comprising: a gas sensor element for detecting the concentration of a specific gas in a gas under measurement; a tubular housing surrounding the gas sensor element and having an opening at a rear end of the housing; a sealing member closing the opening; and a tubular heat dissipating member surrounding the housing and having a rear end located at the same position as the rear end of the housing or located forward of the rear end of the housing, the heat dissipating member reducing the amount of heat transferred from the forward end side of the gas sensor to the sealing member through the housing, wherein the heat dissipating member includes a connection portion connected to the housing on the forward end side of the sealing member, and a main portion extending rearward from the connection portion such that a gap is formed between the main portion and the housing, and the main portion has a heat dissipating opening for establishing communication between the gap and a space on the outer circumferential side of the heat dissipating member, the heat dissipating opening being located rearward of the center of the main portion in the axial direction.

(2) Another gas sensor of the present disclosure is a gas sensor extending in an axial direction from a forward end toward a rear end and comprising: a gas sensor element for detecting the concentration of a specific gas in a gas under measurement; a tubular housing surrounding the gas sensor element and having an opening at a rear end of the housing; a sealing member closing the opening; and a tubular heat dissipating member surrounding the housing and having a rear end located rearward of the rear end of the housing, the heat dissipating member reducing the amount of heat transferred from the forward end side of the gas sensor to the sealing member through the housing, wherein the heat dissipating member includes a connection portion connected to the housing on the forward end side of the sealing member, and a main portion extending rearward from the connection portion such that a gap is formed between the main portion and the housing, and the main portion has a heat dissipating opening for establishing communication between the gap and a space on the outer circumferential side of the heat dissipating member, wherein, when a region where the main portion and the housing overlap each other is defined as an overlapping region, the heat dissipating opening is located rearward of the center of the overlapping region in the axial direction.

Since heat from the forward end of the gas sensor can be dissipated to the outside through the heat dissipating member, the heat transfer to the rear end of the gas sensor can be reduced. Since high-temperature air accumulated in the gap is released to the space on the outer circumferential side of the heat dissipating member through the heat dissipating opening, accumulation of heat in the gap can be avoided. As a result, influence of heat on the rear end portion of the gas sensor can be avoided. For example, influence of heat on the sealing member can be avoided.

(3) Preferably, the length of the heat dissipating opening in the axial direction is greater than a half of the length of the heat dissipating member in the axial direction.

The greater the length of the heat dissipating opening in the axial direction, the greater the ease of release of the high-temperature air accumulated in the gap to the space on the outer circumferential side of the heat dissipating member. Also, in the case where the length of the heat dissipating opening is greater than one-half, the heat dissipating member can have a hole (part of the heat dissipating opening) on the rear end side without fail.

(4) Preferably, the heat dissipating opening gradually increases in width from the forward end side toward the rear end side.

Since the width of the heat dissipating opening increases from the forward end side toward the rear end side, the influence of heat on the rear end portion of the gas sensor can be avoided more reliably. On the forward end side, the ratio of the area of the wall portion is increased for heat transfer, and, on the rear end side, the ratio of the area of the hole is increased for ventilation.

(5) Preferably, the length of the heat dissipating opening in the axial direction is greater than the length of the heat dissipating opening in a direction perpendicular to the axial direction.

(6) Preferably, the housing includes: a metallic shell surrounding the gas sensor element and having a polygonal tool engagement portion and a mounting portion disposed on the rear end side of the tool engagement portion to be continuous with the tool engagement portion; and an outer tube extending rearward from the metallic shell, surrounding the gas sensor element, and including a large diameter portion having a welded portion welded to the mounting portion together with the connection portion, a small diameter portion located rearward of the large diameter portion and being smaller in diameter than the large diameter portion, and a joining portion joining a rear end of the large diameter portion and a forward end of the small diameter portion, wherein a forward end of the heat dissipating opening is located rearward of the welded portion and is located forward of the joining portion.

When water enters a region of the gap on the joining portion side, that water can be drained, through the heat dissipating opening, to the space on the outer circumferential side of the heat dissipating member.

(7) Preferably, when an outer edge of the heat dissipating opening is viewed, a portion of the heat dissipating member on an outer side in a thickness direction thereof has a shape such that a distance between that portion and the widthwise center of the heat dissipating opening gradually decreases toward an inner side in the thickness direction, and a portion of the heat dissipating member on the inner side in the thickness direction has a shape to protrude toward the inner side in the thickness direction.

When a worker performs an operation while grasping the heat dissipating member with his/her fingers from the outer circumferential side, it is possible to prevent catching of the worker's fingers by the edge of the heat dissipating opening.

(8) Preferably, the heat dissipating member has three or more heat dissipating openings formed such that the heat dissipating openings are arranged in a circumferential direction at equal intervals.

Notably, the term "equal" does not mean "equal" in a strict sense and must be interpreted to have a broader meaning within the range in which the effect of the present invention is yielded.

Since three or more heat dissipating openings are arranged in the circumferential direction at equal intervals, the heat dissipation (ventilation) through the heat dissipating opening can be performed more effectively.

(9) Preferably, the heat dissipating member has an inward projecting portion projecting toward a radially inner side, and the inward projecting portion is in contact with the housing in a partial circumferential region.

Since the heat dissipating member can be held while inclination, etc. of the heat dissipating member is prevented by the inward projecting portion, the heat dissipating member can be supported in a stable posture, and deformation of and damage to the heat dissipating member can be prevented more easily.

[Details of the First Embodiment of the Present Disclosure]

A specific example of a gas sensor 100 of a first embodiment of the present disclosure will now be described with reference to the drawings. Notably, the present disclosure is not limited to the example. The scope of the present disclosure is defined by the claims and is intended to include all modifications within the meanings and scopes equivalent to those of the claims.

<Structure of the Gas Sensor>

The gas sensor 100 is an oxygen sensor to be attached to an exhaust pipe 10 of an internal combustion engine. The gas sensor 100 is a so-called full range air-fuel ratio sensor which detects the concentration of oxygen in exhaust gas (gas to be measured) linearly over a range from a rich region to a lean region.

An axial line AX in FIG. 1 is a virtual center axis of the gas sensor 100. The gas sensor 100 has a shape extending in the direction of the axial line AX. The gas sensor 100 includes a gas sensor element 120, a metallic shell 110, an outer tube 103, and a heat dissipating member 104. The gas sensor element 120 outputs a signal corresponding to the concentration of oxygen.

<Structure of the Metallic Shell)

The metallic shell 110 is a tubular metallic member having a through hole H1 extending in the direction of the axial line AX (hereinafter also referred to as the "axial direction"). The metallic shell 110 is disposed radially outward of the gas sensor element 120 so as to surround the gas sensor element 120. The metallic shell 110 plays a role in holding the gas sensor element 120 and a role in fixedly attaching the gas sensor 100 to the exhaust pipe 10.

The metallic shell 110 includes a threaded portion 110A, a tool engagement portion 110B disposed rearward (upward in the drawing sheet) of the threaded portion 110A, a protector connection portion 110C disposed forward (downward in the drawing sheet) of the threaded portion 110A, and a mounting portion 110D disposed rearward of the tool engagement portion 110B. The exhaust pipe 10 has a thread groove 20 for attachment of the gas sensor 100. By fastening the threaded portion 110A to the thread groove 20 of the exhaust pipe 10, the gas sensor 100 is fixed to the exhaust pipe 10.

The tool engagement portion 110B has a regular hexagonal outer shape as viewed from the rear end side of the gas sensor 100. To attach the gas sensor 100 to a vehicle, a tool (not shown) such as a spanner or a socket wrench is engaged with the tool engagement portion 110B. By rotationally moving the tool engaged with the tool engagement portion 110B, the threaded portion 110A is fastened to the thread groove 20.

<Structure of Protectors>

A pair of protectors (i.e., an inner protector 101 and an outer protector 102) are fixed integrally to the protector connection portion 110C of the metallic shell 110 by laser welding (the welded portion is a portion hatched with dots). The inner protector 101 is disposed inside the outer protector 102. The inner protector 101 has a closed-end tubular shape and has an opening on the rear end side. Meanwhile, the outer protector 102 has a tubular shape and has openings on the forward end side and the rear end side, respectively. The inner protector 101 and the outer protector 102 have a plurality of introduction holes 101C and a plurality of introduction holes 102C, respectively. The plurality of introduction holes 101C are provided in a circumferential wall portion of the inner protector 101, and the plurality of introduction holes 102C are provided in a circumferential wall portion of the outer protector 102.

In a state in which the gas sensor 100 is attached to the exhaust pipe 10 of the vehicle, the exhaust gas in the exhaust pipe 10 is introduced into a space inside the outer protector 102 through the introduction holes 102C of the outer protector 102. The exhaust gas introduced into the space inside the outer protector 102 is introduced into a space inside the inner protector 101 through the introduction holes 101C of the inner protector 101.

<Structure of the Outer Tube>

The outer tube 103 includes, sequentially from the forward end side, a connection portion 103A, a separator housing portion 103B, a lead wire housing portion 103C, and a sealing member holding portion 103D. Also, the outer tube 103 includes a joining portion 103G for joining the rear end of the connection portion 103A and the forward end of the separator housing portion 103B. The joining portion 103G extends perpendicularly to the direction of the axial line AX.

The outer tube 103 is formed of metal and is formed of SUS304 in the present embodiment. The outer tube 103 has a tubular overall shape. The connection portion 103A has a larger diameter than the separator housing portion 103B, and the separator housing portion 103B has a larger diameter than the lead wire housing portion 103C. The lead wire housing portion 103C has a larger diameter than the sealing member holding portion 103D. The separator housing portion 103B is connected to the lead wire housing portion 103C through a step portion 103F. The inner circumferential surface of the connection portion 103A is in contact with the outer circumferential surface of the mounting portion 110D of the metallic shell 110. The connection portion 103A is fixed to the mounting portion 110D by laser welding. A portion welded by laser welding will be referred to as the welded portion 105. The welded portion 105 is a portion hatched with dots in FIG. 1.

An opening 103E is formed at the rear end of the sealing member holding portion 103D of the outer tube 103. Three sensor lead wires 193 and two heater lead wires 194 are introduced through the opening 103E into the outer tube 103. The lead wires 193 and 194 play a role in electrically connecting the gas sensor 100 to an external control circuit.

A sealing member 191 such as a grommet is attached to the sealing member holding portion 103D of the outer tube 103. The sealing member 191 is formed of rubber such as silicon rubber or fluororubber and is formed of fluororubber in the present embodiment. The opening 103E of the outer tube 103 is closed by the sealing member 191, whereby the interior space of the outer tube 103 is sealed. The lead wires 193 and 194 pass through the sealing member 191 and are introduced into the separator housing portion 103B through the lead wire housing portion 103C of the outer tube 103.

<Structure of the Gas Sensor Element>

The gas sensor element 120 has a layered structure including elongated plate members stacked together. The gas sensor element 120 has a quadrangular prism shape, and its cross section perpendicular to the axial line AX has an approximately rectangular shape. The gas sensor element 120 is fixed to the metallic shell 110 at the position of the through hole H1 of the metallic shell 110. The gas sensor element 120 is housed in the gas sensor 100 so as to extend in the direction of the axial line AX. The gas sensor element 120 is disposed coaxially with the tool engagement portion 110B of the metallic shell 110. The tool engagement portion 110B is disposed so as to surround the gas sensor element 120.

A gas detection portion 121 is provided at the forward end of the gas sensor element 120. The gas detection portion 121 is configured to be capable of detecting the concentration of oxygen in the exhaust gas. The gas detection portion 121 is disposed inside the inner protector 101. In a state in which the gas sensor 100 is attached to the exhaust pipe 10 of the vehicle, the gas detection portion 121 is exposed to the exhaust gas introduced into the space inside the inner protector 101 through the plurality of introduction holes 101C and 102C. The concentration of oxygen in the exhaust gas is thereby detected by the gas detection portion 121.

<Structure of a Separator>

A separator 181 is housed in the separator housing portion 103B of the outer tube 103. The separator 181 is a tubular insulating member having a through hole H2. The through hole H2 is formed to extend in the direction of the axial line AX. A tubular urging metal member 190 is disposed on the outer circumference of the separator 181. The separator 181 is urged toward the sealing member 191 by the urging metal member 190. As a result, the separator 181 is held in the separator housing portion 103B in a state in which the separator 181 is pressed against the step portion 103F of the outer tube 103. A rear end portion of the gas sensor element 120 is housed in the through hole H2 of the separator 181.

Three sensor electrode pads (not shown) and two heater electrode pads (not shown) are disposed on the rear end portion of the gas sensor element 120. Meanwhile, three sensor connection terminals 182 and two heater connection terminals 183 are housed in the separator 181. The connection terminals 182 and 183 each have a flat spring bent from the forward end side of the gas sensor 100 toward the rear end side. The elastic forces of the flat springs bring the connection terminals 182 and 183 into elastic contact with the respective electrode pads. The connection terminals 182 and 183 are electrically connected to the respective lead wires 193 and 194.

<Structure for Fixing the Gas Sensor Element>

The gas sensor element 120 is fixed to the metallic shell 110 in the following manner. A ceramic holder 111, a powder filled layer 112, and a ceramic sleeve 113 are stacked in the through hole H1 of the metallic shell 110 in this order from the forward end side to the rear end side.

The ceramic holder 111 is formed of alumina ($Al_2O_3$). A crimp ring 114 is disposed between the ceramic sleeve 113 and the rear end portion of the metallic shell 110. A rectangular through hole H3 is formed at the center of the ceramic holder 111. The through hole H3 of the ceramic holder 111 extends in the direction of the axial line AX. The gas sensor element 120 is inserted into the through hole H3 of the ceramic holder 111.

The powder filled layer 112 is formed by filling talc powder above the ceramic holder 111. The ceramic sleeve 113 is disposed on the powder filled layer 112. A rectangular through hole H4 is formed at the center of the ceramic sleeve 113. The gas sensor element 120 is inserted into the through hole H4 of the ceramic sleeve 113. The ceramic sleeve 113 is formed of alumina. A rear end portion of the metallic shell 110 is crimped by bending the rear end portion radially inward, so that the ceramic sleeve 113 is pressed toward the powder filled layer 112 through the crimp ring 114. In this manner, the gas sensor element 120 integrated with the ceramic holder 111, the powder filled layer 112, and the ceramic sleeve 113 is fixed to the metallic shell 110.

<Structure of the Heat Dissipating Member>

The heat dissipating member 104 includes a connection portion 104A and a main portion 104B. The connection portion 104A is connected to the metallic shell 110 on the forward end side of the sealing member 191. The main portion 104B extends rearward from the connection portion 104A, and a gap S is formed between the main portion 104B and the outer tube 103. The heat dissipating member 104 has a tubular shape and surrounds the outer tube 103. The heat dissipating member 104 is formed of metal. In the present embodiment, the heat dissipating member 104 is formed of SUS304, which is the same material as that of the outer tube 103. The connection portion 104A is disposed on the forward end side of the main portion 104B to be continuous with the main portion 104B. In the direction of the axial line AX, the rear end of the main portion 104B is located at the same position as the forward end of the sealing member 191 and is located rearward of the rear end of the separator housing portion 103B.

The heat dissipating member 104 has a larger thickness and a larger outer diameter than the outer tube 103. The heat transfer resistance per unit length of the outer tube 103 in the direction of the axial line AX of the gas sensor 100 is larger than that of the heat dissipating member 104. Therefore, the amount of heat transfer from the forward end side of the gas sensor 100 to the heat dissipating member 104 is larger than the amount of heat transfer to the outer tube 103.

The heat dissipating member 104 is disposed coaxially with the tool engagement portion 110B. The outer circumferential surface of the heat dissipating member 104 is located radially inward of the tool engagement portion 110B (on the side toward the axial line AX) when viewed from the rear end side of the gas sensor 100. The inner circumferential surface of the heat dissipating member 104 is located radially outward of the mounting portion 110D when viewed from the rear end side of the gas sensor 100. The connection portion 104A and the main portion 104B have the same maximum diameter D1. The maximum diameter D1 of the connection portion 104A and the main portion 104B is smaller than the smallest diameter D2 of the tool engagement portion 110B.

The inner circumferential surface of the connection portion 104A is in contact with the outer circumferential surface of the connection portion 103A of the outer tube 103. The connection portion 104A is integrally fixed by laser welding to the mounting portion 110D of the metallic shell 110 through the connection portion 103A of the outer tube 103 (the welded portion 105 is a portion hatched with dots).

Figure 2:
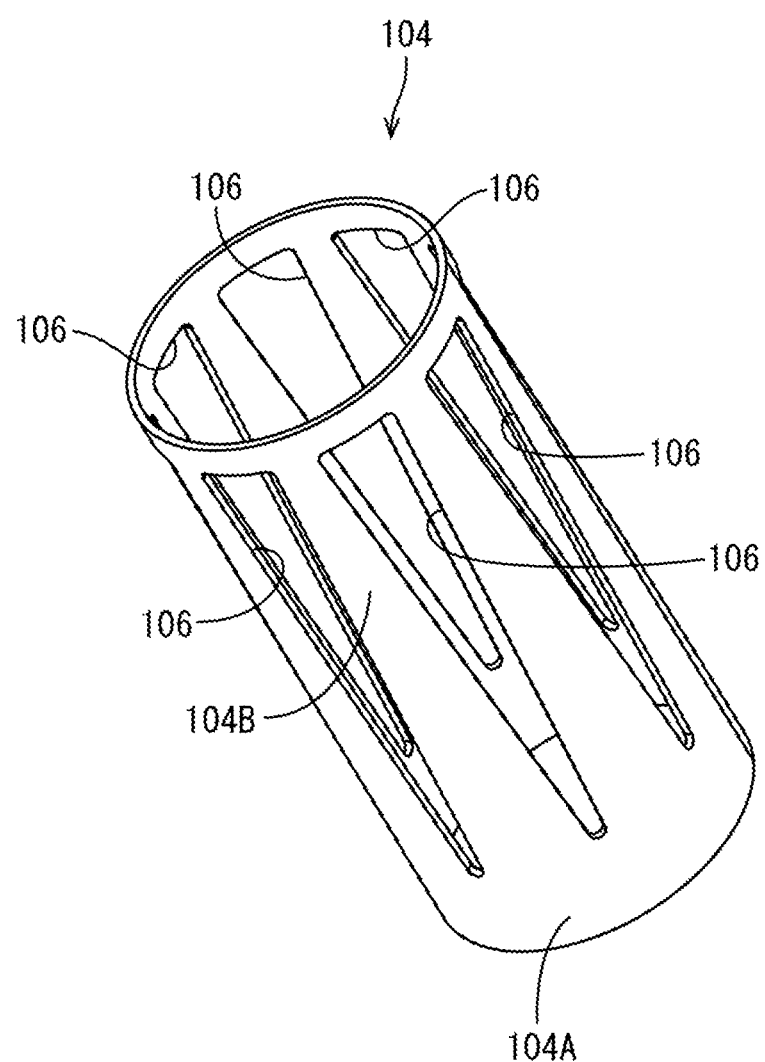
FIG. 2 is a perspective view of a heat dissipating member according to the first embodiment of the present disclosure.

The main portion 104B has heat dissipating openings 106, through which the gap S communicates with a space on the outer circumferential side of the heat dissipating member 104. The heat dissipating openings 106 are provided in a region including at least a part of the main portion 104B located rearward of the center of the main portion 104B in the direction of the axial line AX. In the present embodiment, the heat dissipating openings 106 are provided in a region extending from the forward end of the main portion 104B to a position immediately before the rear end of the main portion 104B. As shown in FIG. 2, each heat dissipating opening 106 has the shape of an inverted triangle whose base is located at the rear end and whose apex is located at the forward end, and the width of each heat dissipating opening 106 gradually increases from the forward end side toward the rear end side. The heat dissipating openings 106, the number of which is three or more, are disposed at equal intervals in the circumferential direction. In the present embodiment, eight heat dissipating openings 106 are provided in the main portion 104B.

The length of each heat dissipating opening 106 in the direction of the axial line AX is greater than a half of the length of the heat dissipating member 104 in the direction of the axial line AX. The length of each heat dissipating opening 106 in the direction of the axial line AX is greater than the length of each heat dissipating opening 106 in a direction perpendicular to the direction of the axial line AX. The forward end of each heat dissipating opening 106 is located rearward of the welded portion 105 and is located forward of the joining portion 103G.

The heat dissipating openings 106 are formed by punching a metal plate, which is a base material, from the outer side toward the inner side in the thickness direction. Therefore, a burr 104c produced as a result of the punching projects toward the inner side in the thickness direction. As illustrated in FIG. 1, when the edge of each heat dissipating opening 106 is viewed, a portion of the heat dissipating member 104 on the outer side in the thickness direction has a shape such that the distance between that portion and the widthwise center of the heat dissipating opening 106 gradually decreases toward the inner side in the thickness direction, and a portion of the heat dissipating member 104 on the inner side in the thickness direction has a shape to protrude toward the inner side in the thickness direction to form the burr 104c.

<Action of the Heat Dissipating Member>

The protective action of the heat dissipating member 104 is as follows. Since the connection portion 104A of the heat dissipating member 104 is connected to the connection portion 103A of the outer tube 103, the main portion 104B covers the separator housing portion 103B, and the separator housing portion 103B is thereby protected by the main portion 104B. This prevents application of impact onto the urging metal member 190 disposed inside the separator housing portion 103B, thereby preventing occurrence of a situation in which the impact transmits to the separator 181 held by the urging metal member 190 and the connection terminals 182 and 183 attached to the separator 181 shift, resulting in breakage of electrical connections between the electrode pads and the connection terminals 182 and 183.

The heat dissipation action of the heat dissipating member 104 is as follows. The heat of the gas sensor 100 transfers from the connection portion 103A of the outer tube 103 to both the separator housing portion 103B and the connection portion 104A of the heat dissipating member 104. However, the heat transfer resistance of the separator housing portion 103B is larger than the heat transfer resistance of the connection portion 104A of the heat dissipating member 104. Therefore, the heat from the forward end side of the gas sensor 100 transfers from the connection portion 103A of the outer tube 103 through the connection portion 104A of the heat dissipating member 104 to the main portion 104B and is then dissipated to the outside from the main portion 104B. Thus, the amount of heat transferred to the sealing member holding portion 103D is reduced, so that thermal degradation of the sealing member 191 is suppressed.

When the heat capacity of the heat dissipating member is increased, the heat dissipating performance of the heat dissipating member is enhanced, and the performance of dissipating heat from the heat dissipating member 104 to the outer circumferential side is enhanced. However, since the performance of dissipating heat from the heat dissipating member 104 to the inner circumferential side is also enhanced, heat is more likely to accumulate in the gap S. In order to solve such a problem, in the present embodiment, the heat dissipating openings 106 are provided so as to release the heat accumulated in the gap S to the outside. As a result, the heat accumulated in the gap S is restrained from being transferred to the sealing member holding portion 103D, whereby thermal deterioration of the sealing member 191 is suppressed.

<Effects of the Present Embodiment>

As described above, the gas sensor 100 of the present embodiment extends in the direction of the axial line AX from the forward end toward the rear end and includes the gas sensor element 120 which detects the concentration of a specific gas in a gas under measurement, the tubular housing 130 which surrounds the gas sensor element 120 and has an opening 103E at the rear end, the sealing member 191 which closes the opening 103E, and the tubular heat dissipating member 104 which surrounds the housing, whose rear end is located at the same position as the rear end of the housing or located forward of the rear end of the housing, and which reduces the amount of heat transferred from the forward end side of the gas sensor 100 to the sealing member 191 through the housing. The heat dissipating member 104 has the connection portion 104A connected to the housing on the forward end side of the sealing member 191, and the main portion 104B which extends rearward from the connection portion 104A such that the gap S is formed between the main portion 104B and the housing. The main portion 104B has the heat dissipating openings 106 which are located rearward of the center of the main portion 104B in the direction of the axial line AX and which establish communication between the gap S and the space on the outer circumferential side of the heat dissipating member 104.

Since the above-described structure enables dissipation of heat from the forward end of the gas sensor 100 to the outside through the heat dissipating member 104, the heat transfer to the rear end of the gas sensor 100 can be reduced. Since the high-temperature air accumulated in the gap S is released to the space on the outer circumferential side of the heat dissipating member 104 through the heat dissipating openings 106, accumulation of heat in the gap S can be avoided. As a result, influence of heat on the rear end portion of the gas sensor 100 can be avoided. For example, influence of heat on the sealing member 191 can be avoided.

The length of the heat dissipating openings 106 in the direction of the axial line AX is preferably greater than a half of the length of the heat dissipating member 104 in the direction of the axial line AX.

The greater the length of the heat dissipating openings 106 in the direction of the axial line AX, the greater the ease of release of the high-temperature air accumulated in the gap S to the space on the outer circumferential side of the heat dissipating member 104. Also, in the case where the length of the heat dissipating openings 106 is greater than one-half, the heat dissipating member 104 can have holes (parts of the heat dissipating openings 106) on the rear end side without fail.

Preferably, each heat dissipating opening 106 is formed such that its width increases gradually from the forward end side toward the rear end side.

Since the width of each heat dissipating opening 106 increases from the forward end side toward the rear end side, the influence of heat on the rear end portion of the gas sensor 100 can be avoided more reliably. On the forward end side, the ratio of the area of the wall portion is increased for heat transfer, and, on the rear end side, the ratio of the area of the holes is increased for ventilation.

Preferably, the length of each heat dissipating opening 106 in the direction of the axial line AX is greater than the length of each heat dissipating opening 106 in the direction perpendicular to the direction of the axial line AX.

Figure 10:
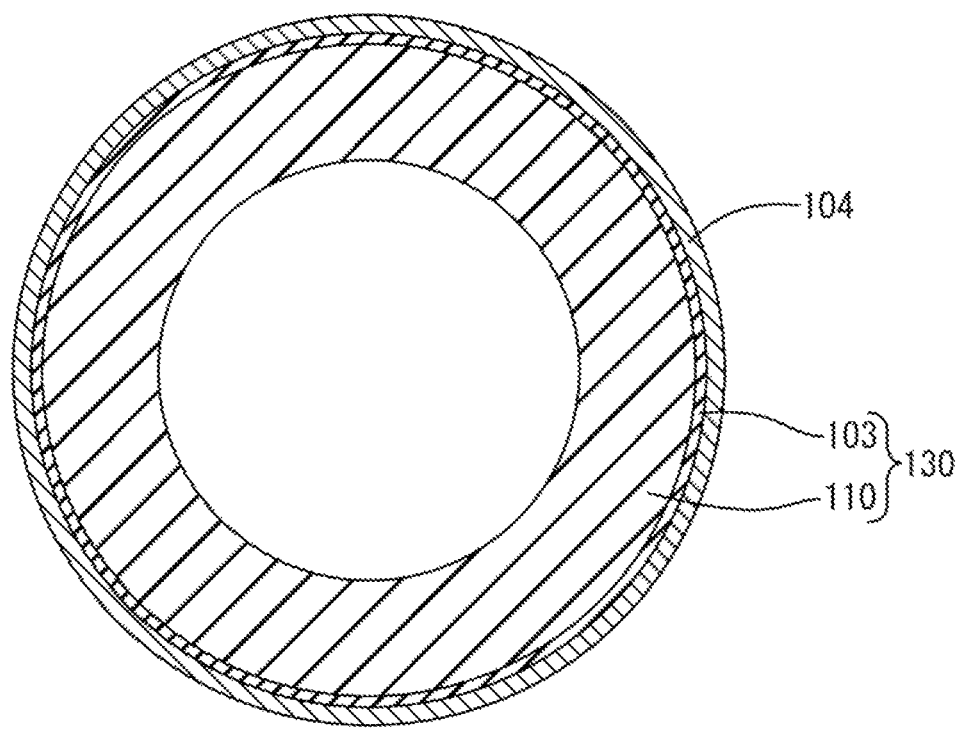
FIG. 10 is a simplified view of FIG. 1 that is cross-sectioned at A-A showing only the tubular housing (outer tube and metallic shell) and the heat dissipating member.

Preferably, the housing 130 is composed of the metallic shell 110 and the outer tube 103. See FIG. 10. The metallic shell 110 surrounds the gas sensor element 120 and includes the polygonal tool engagement portion 110B and the mounting portion 110D disposed on the rear end side of the tool engagement portion 110B to be continuous with the tool engagement portion 110B. The outer tube 103 extends rearward from the metallic shell 110 and surrounds the gas sensor element 120. The outer tube 103 includes a large diameter portion having the welded portion 105 welded to the mounting portion 110D together with the connection portion 104A, a small diameter portion disposed on the rear end side of the large diameter portion and having a diameter smaller than that of the large diameter portion, and the joining portion 103G joining the rear end of the large diameter portion and the forward end of the small diameter portion. The forward end of each heat dissipating opening 106 is located rearward of the welded portion 105 and is located forward of the joining portion 103G.

When water enters a region of the gap S on the joining portion 103G side, that water can be drained, through the heat dissipating openings 106, to the space on the outer circumferential side of the heat dissipating member 104.

Preferably, when the edge of each heat dissipating opening 106 is viewed, a portion of the heat dissipating member 104 on the outer side in the thickness direction has a shape such that the distance between that portion and the widthwise center of the heat dissipating opening 106 gradually decreases toward the inner side in the thickness direction, and a portion of the heat dissipating member 104 on the inner side in the thickness direction has a shape to protrude toward the inner side in the thickness direction.

When a worker performs an operation while grasping the heat dissipating member 104 with his/her fingers from the outer circumferential side, it is possible to prevent catching of the worker's fingers by the edges of the heat dissipating openings 106.

Preferably, the number of the heat dissipating openings 106 is three or more, and the heat dissipating openings 106 are disposed at equal intervals in the circumferential direction.

Since three or more heat dissipating openings are disposed at equal intervals in the circumferential direction, the heat dissipation (ventilation) through the heat dissipating openings 106 can be performed more effectively.

[Details of a Second Embodiment of the Present Disclosure]

A specific example of a gas sensor 200 of a second embodiment of the present disclosure will now be described with reference to the drawings. Notably, the present disclosure is not limited to the example. The scope of the present disclosure is defined by the claims and is intended to include all modifications within the meanings and scopes equivalent to those of the claims.

The gas sensor 200 of the second embodiment of the present disclosure uses a heat dissipating member 204 which has a shape different from the shape of the heat dissipating member 104 of the first embodiment. Since the remaining structure is the same as that in the first embodiment, its description will not be repeated. The same structural portions as those in the first embodiment are denoted by the same reference numerals as those in the first embodiment, and structural portions corresponding to those in the first embodiment are denoted by reference numerals obtained by changing the hundred-place digits (which are 1) of the respective reference numerals used in the first embodiment to 2.

Figure 4:
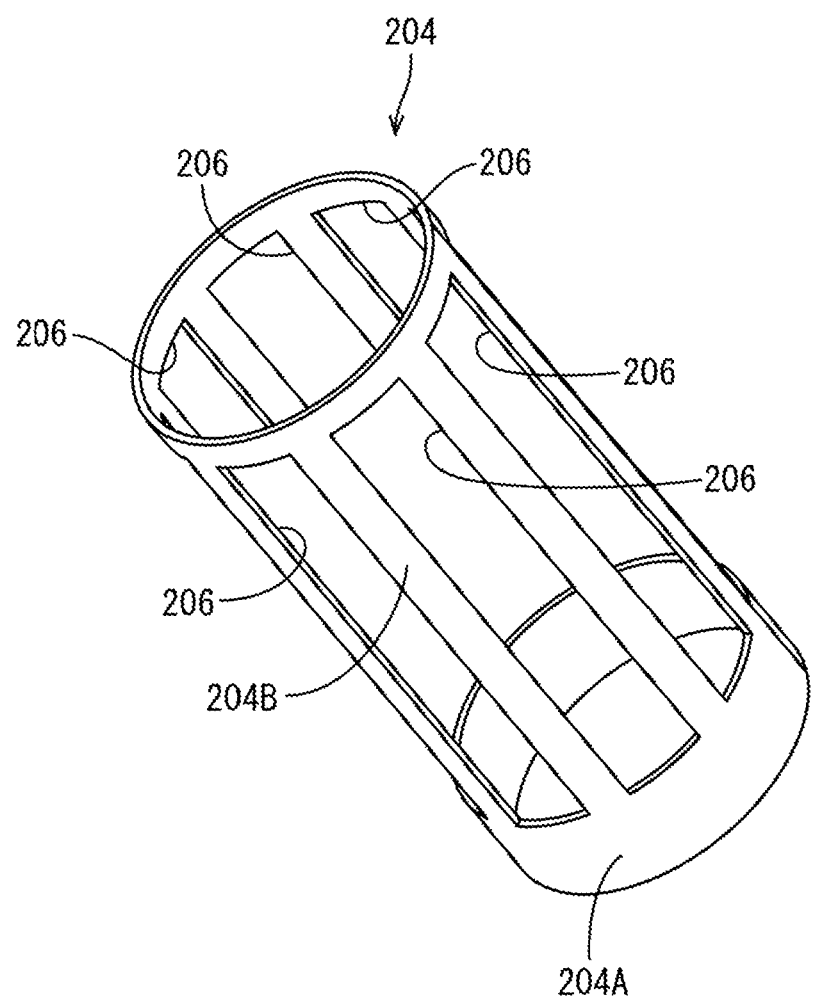
FIG. 4 is a perspective view of a heat dissipating member according to the second embodiment of the present disclosure.

The heat dissipating member 204 of the second embodiment of the present disclosure has a cylindrical shape and opens toward the forward end side and the rear end side. As shown in FIG. 4, the heat dissipating member 204 includes a connection portion 204A located on the forward end side and having a cylindrical shape, and a main portion 204B extending rearward from the rear end of the connection portion 204A in such a manner as to form a cylindrical shape and have the same diameter as the connection portion 204A.

The main portion 204B has a plurality of heat dissipating openings 206 arranged in the circumferential direction. The heat dissipating openings 206 are provided in a region including at least a part of the main portion 204B located rearward of the center of the main portion 204B in the direction of the axial line AX. In the present embodiment, the heat dissipating openings 206 are provided in a region extending from the forward end of the main portion 204B to a position immediately before the rear end of the main portion 204B. Each heat dissipating opening 206 has the shape of a rectangle whose short sides are located at the rear end and the forward end, and has a constant width from the forward end side toward the rear end side. The heat dissipating openings 206, the number of which is three or more, are disposed at equal intervals in the circumferential direction. In the present embodiment, eight heat dissipating openings 206 are provided in the main portion 204B.

Figure 3:
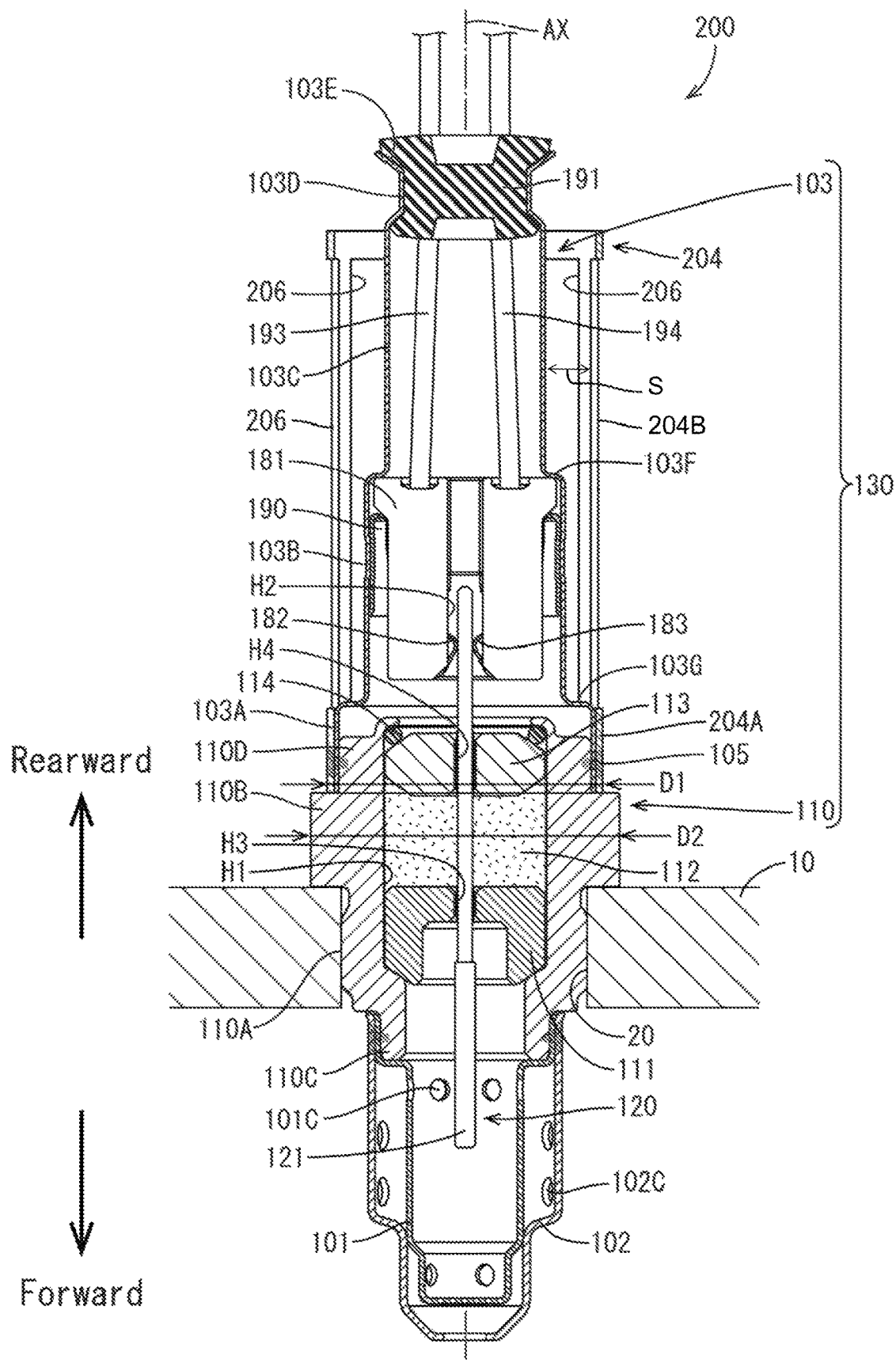
FIG. 3 is a cross-sectional view showing an internal structure of a gas sensor according to a second embodiment of the present disclosure.

As shown in FIG. 3, the length of each heat dissipating opening 206 in the direction of the axial line AX is greater than a half of the length of the heat dissipating member 204 in the direction of the axial line AX. The length of each heat dissipating opening 206 in the direction of the axial line AX is greater than the length of each heat dissipating opening 206 in a direction perpendicular to the direction of the axial line AX. The forward end of each heat dissipating opening 206 is located rearward of the welded portion 105 and is located forward of the joining portion 103G.

The heat dissipating openings 206 are formed by punching a metal plate, which is a base material, from the outer side toward the inner side in the thickness direction. Therefore, a burr produced as a result of the punching projects toward the inner side in the thickness direction. Similar to the First embodiment as illustrated in FIG. 1, when the edge of each heat dissipating opening 206 is viewed, a portion of the heat dissipating member 204 on the outer side in the thickness direction has a shape such that the distance between that portion and the widthwise center of the heat dissipating opening 206 gradually decreases toward the inner side in the thickness direction, and a portion of the heat dissipating member 204 on the inner side in the thickness direction has a shape to protrude toward the inner side in the thickness direction.

Since the heat dissipating openings 206 of the second embodiment of the present disclosure are greater in opening area than the heat dissipating openings 106 of the first embodiment, the high-temperature air accumulated in the gap S is released to the space on the outer circumferential side of the heat dissipating member 204 through the heat dissipating openings 206. Therefore, accumulation of heat in the gap S can be avoided more reliably.

[Details of a Third Embodiment of the Present Disclosure]

A specific example of a gas sensor 300 of a third embodiment of the present disclosure will now be described with reference to the drawings. Notably, the present disclosure is not limited to the example. The scope of the present disclosure is defined by the claims and is intended to include all modifications within the meanings and scopes equivalent to those of the claims.

The gas sensor 300 of the third embodiment of the present disclosure uses a heat dissipating member 304 which has a shape different from the shape of the heat dissipating member 104 of the first embodiment. Since the remaining structure is the same as that in the first embodiment, its description will not be repeated. The same structural portions as those in the first embodiment are denoted by the same reference numerals as those in the first embodiment, and structural portions corresponding to those in the first embodiment are denoted by reference numerals obtained by changing the hundred-place digits (which are 1) of the respective reference numerals used in the first embodiment to 3.

The heat dissipating member 304 of the third embodiment of the present disclosure includes a heat dissipating outer tube 330 and a heat blocking cover 340. Both the heat dissipating outer tube 330 and the heat blocking cover 340 are formed of metal. In the present embodiment, the heat dissipating outer tube 330 and the heat blocking cover 340 are formed of SUS304, which is the same material as the material of the outer tube 103.

Figure 6:
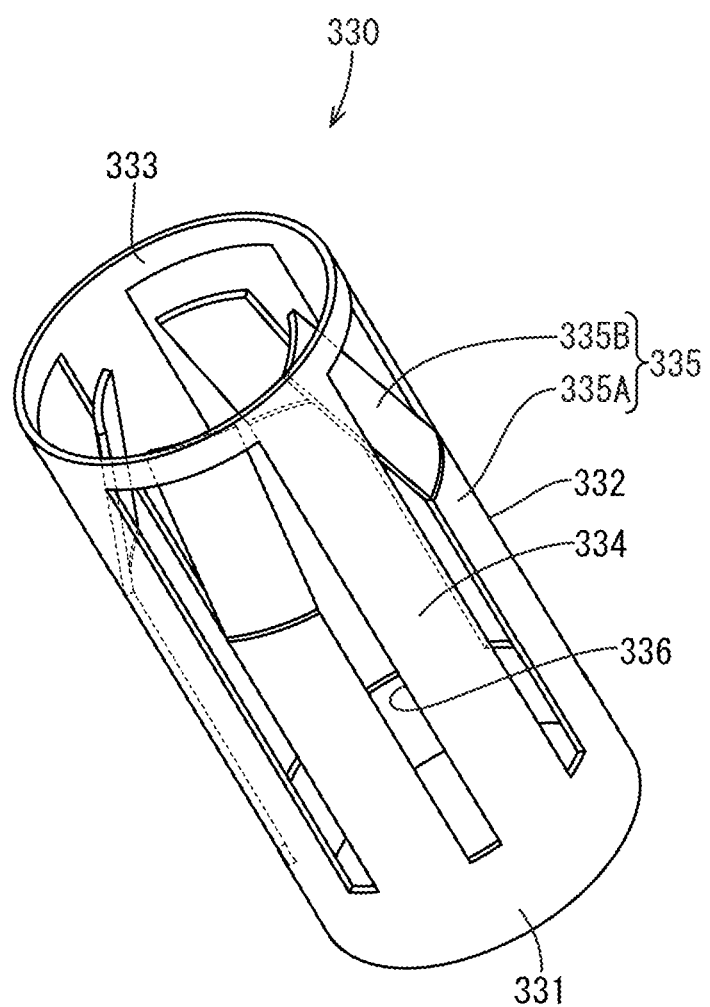
FIG. 6 is a perspective view of a heat dissipating outer tube according to the third embodiment of the present disclosure.

The heat dissipating outer tube 330 of the third embodiment of the present disclosure has a cylindrical shape and opens toward the forward end side and the rear end side. As shown in FIG. 6, the heat dissipating outer tube 330 includes a connection portion 331 located on the forward end side and having a cylindrical shape, a joining portion 333 located on the rear end side and having a cylindrical shape, and a main portion 332 connecting the connection portion 331 and the joining portion 333. The main portion 332 has a plurality of heat dissipating openings 336 arranged in the circumferential direction. The heat dissipating openings 336 are provided in a region including at least a part of the main portion 332 located rearward of the center of the main portion 332 in the direction of the axial line AX. In the present embodiment, the heat dissipating openings 336 are provided in a region extending over the entirety of the main portion 332.

The main portion 332 has a plurality of stationary pieces 334, and each stationary piece 334 is located between a pair of heat dissipating openings 336 located adjacent to each other. Namely, the plurality of stationary pieces 334 and the plurality of heat dissipating openings 336 are arranged alternatingly. The stationary pieces 334 are portions which extend straight from the connection portion 331 toward the joining portion 333 and join the rear end of the connection portion 331 and the forward end of the joining portion 333. Each stationary piece 334 has the shape of a rectangle whose short sides are located at the rear end and the forward end, and has a constant width from the forward end side toward the rear end side.

Each heat dissipating opening 336 has a constant width from the forward end side toward the rear end side. The heat dissipating openings 336, the number of which is three or more, are disposed at equal intervals in the circumferential direction. In the present embodiment, four heat dissipating openings 336 and four stationary pieces 334 are provided in the main portion 332.

A flexible piece 335 cantilevered and projecting rearward is disposed in each heat dissipating opening 336. The rear end of the flexible piece 335 can be elastically displaced outward in the radial direction of the main portion 332. The flexible piece 335 includes a straight portion 335A extending straight rearward from the rear end of the connection portion 331, and an inclined portion 335B extending rearward from the rear end of the straight portion 335A while inclining toward the radially inner side.

Figure 5:
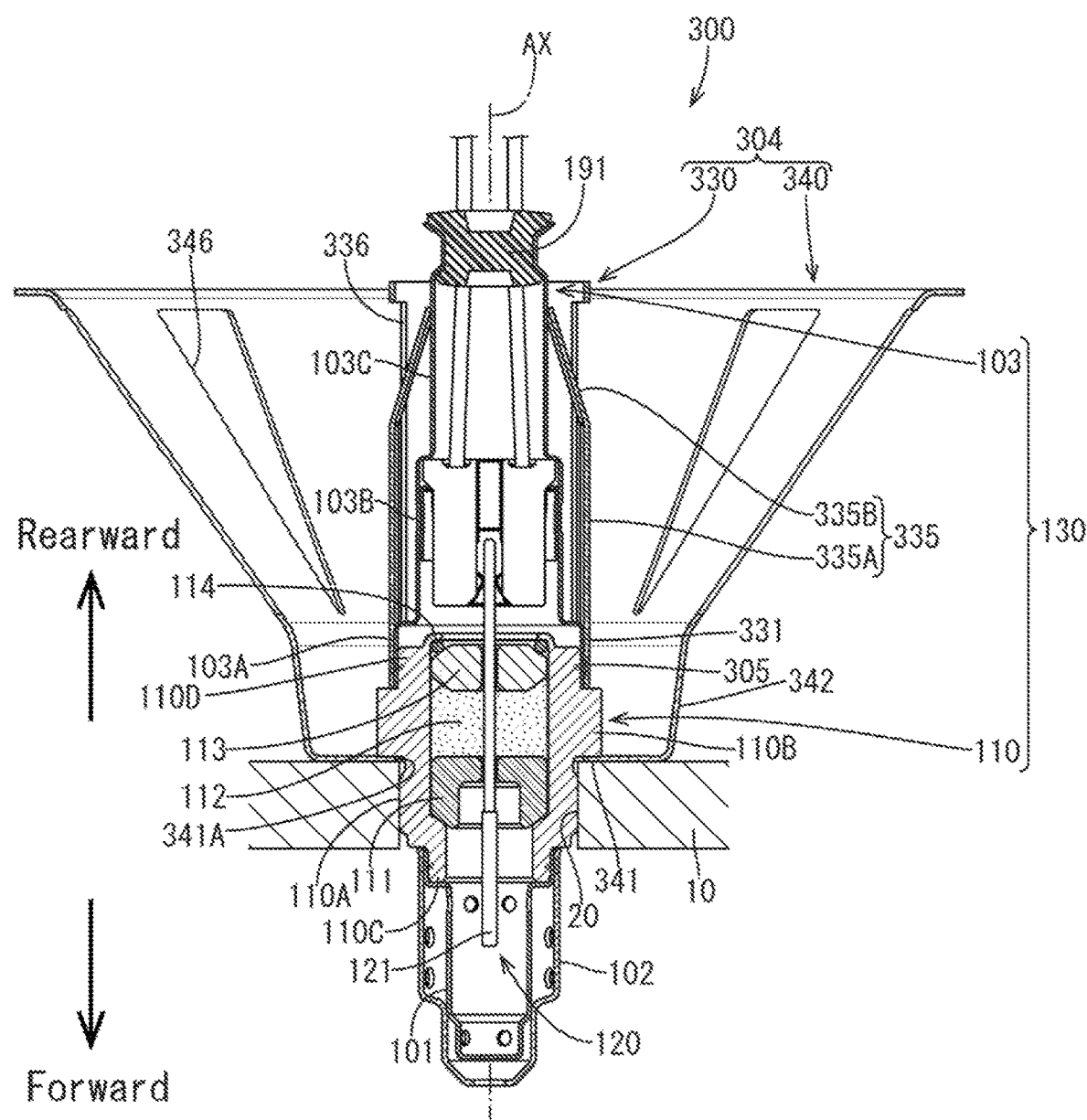
FIG. 5 is a cross-sectional view showing an internal structure of a gas sensor according to a third embodiment of the present disclosure.

The inner circumferential surface of the connection portion 331 is in contact with the outer circumferential surface of the connection portion 103A of the outer tube 103. The connection portion 331 is integrally fixed, by laser welding, to the mounting portion 110D of the metallic shell 110 via the connection portion 103A of the outer tube 103. A portion welded by laser welding will be referred to as the welded portion 305. The welded portion 305 is a portion hatched with dots in FIG. 5.

The inclined portion 335B of each flexible piece 335 is in contact with the lead wire housing portion 103C of the outer tube 103 in a partial circumferential region. Since the plurality of flexible pieces 335 are disposed to surround the outer tube 103 and the heat dissipating outer tube 330 is disposed to extend along the axial line AX, the heat dissipating outer tube 330 is disposed coaxially with the outer tube 103, whereby the heat dissipating outer tube 330 is prevented from approaching the outer tube 103. Since the heat dissipating outer tube 330 protrudes from the connection portion 103A of the outer tube 103 in a cantilevered fashion, the heat dissipating outer tube 330 tends to incline toward the outer tube 103 so that the joining portion 333 approaches the outer tube 103. Such inclination of the heat dissipating outer tube 330 can be effectively prevented by the inclined portions 335B of the flexible pieces 335.

Figure 7:
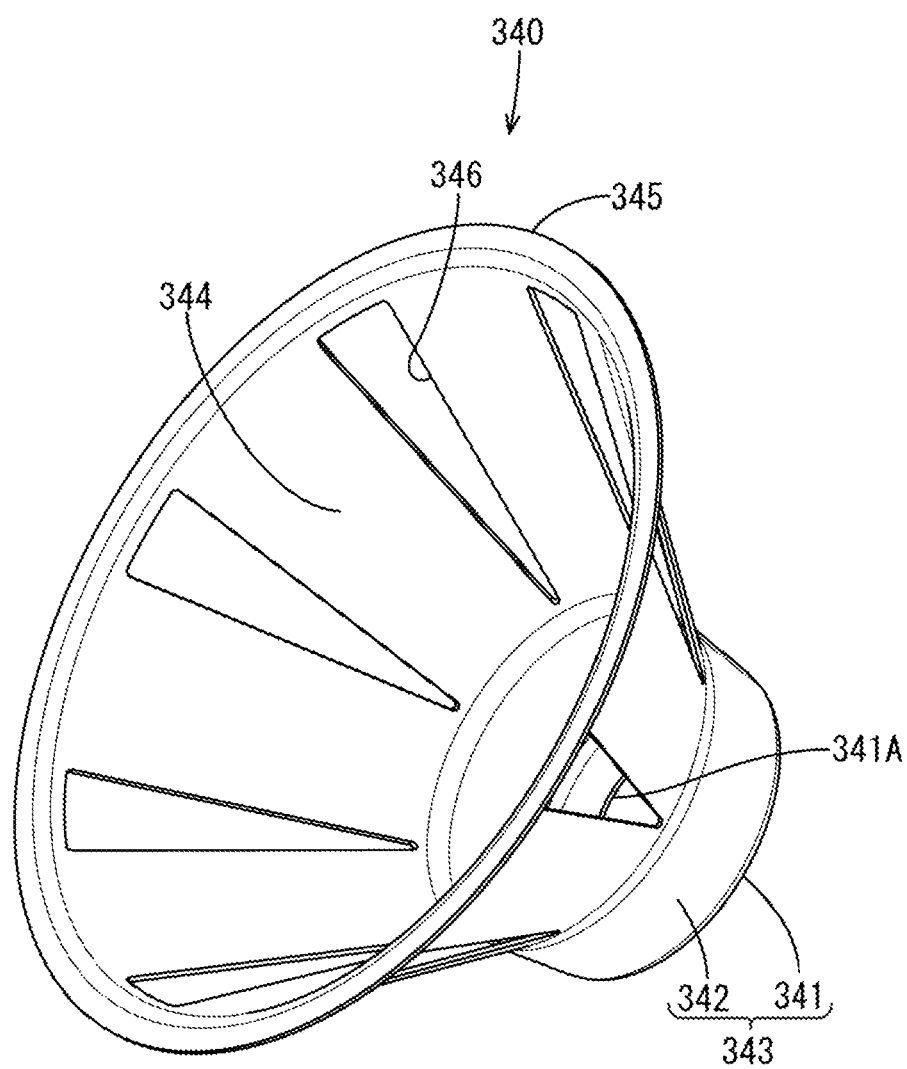
FIG. 7 is a perspective view of a heat blocking cover according to the third embodiment of the present disclosure.

As shown in FIG. 7, the heat blocking cover 340 includes a connection portion 343, a diameter increasing portion 344, and a flange portion 345. The connection portion 343 includes a bottom wall portion 341 and a tubular portion 342 projecting rearward from the circumferential edge of the bottom wall portion 341. The diameter increasing portion 344 extends rearward from the rear end of the tubular portion 342 while inclines outward such that the diameter of the diameter increasing portion 344 increases. The flange portion 345 extends from the rear end of the diameter increasing portion 344 toward the radially outer side.

The bottom wall portion 341 has an insertion hole 341A through which the threaded portion 110A of the metallic shell 110 is inserted. A hole edge portion of the bottom wall portion 341 around the insertion hole 341A is held between a surface of the tool engagement portion 110B on the forward end side and a portion of the exhaust pipe 10 around the edge of the opening of the thread groove 20. As a result, the heat blocking cover 340 is held by the tool engagement portion 110B.

The tubular portion 342 is located on the radially outer side of the tool engagement portion 110B of the metallic shell 110. A predetermined clearance is provided between the tubular portion 342 and the tool engagement portion 110B, and this clearance serves as a space in which a tool such as a socket is fitted onto the tool engagement portion 110B.

The diameter increasing portion 344 is located on the radially outer side of the separator housing portion 103B and the lead wire housing portion 103C of the outer tube 103. The diameter increasing portion 344 has a plurality of heat dissipating openings 346 arranged in the circumferential direction. The heat dissipating openings 346 are provided in a region including at least a part of the diameter increasing portion 344 located rearward of the center of the diameter increasing portion 344 in the direction of the axial line AX. In the present embodiment, the heat dissipating openings 346 are provided in a region extending over the entirety of the diameter increasing portion 344. As shown in FIG. 7, each heat dissipating opening 346 has the shape of an inverted triangle whose base is located at the rear end and whose apex is located at the forward end, and the width of each heat dissipating opening 346 gradually increases from the forward end side toward the rear end side.

The heat blocking cover 340 has a function of blocking the heat transferred from the exhaust pipe 10 and a function of dissipating the heat from the forward end of the gas sensor 300 to the outside. Since the diameter of the diameter increasing portion 344 increases from the forward end side toward the rear end side, heat is less likely to accumulate between the diameter increasing portion 344 and the heat dissipating outer tube 330. Heat (if any) accumulated between the diameter increasing portion 344 and the heat dissipating outer tube 330 is released to the space on the outer circumferential side of the diameter increasing portion 344 through the heat dissipating openings 346. Therefore, accumulation of heat can be avoided.

As described above, the heat dissipating outer tube 330 of the heat dissipating member 304 of the present embodiment has the inclined portions 335B projecting toward the radially inner side, and, in partial regions in the circumferential direction, the inclined portions 335B are in contact with the lead wire housing portion 103C of the outer tube 103.

Since the heat dissipating outer tube 330 of the heat dissipating member 304 can be held while inclination, etc. of the heat dissipating outer tube 330 is prevented by the inclined portions 335B, the heat dissipating outer tube 330 can be supported in a stable posture, and deformation of and damage to the heat dissipating outer tube 330 can be prevented more easily.

[Details of a Fourth Embodiment of the Present Disclosure]

A specific example of a heat dissipating outer tube 430 of a fourth embodiment of the present disclosure will now be described with reference to the drawings. Notably, the present disclosure is not limited to the example. The scope of the present disclosure is defined by the claims and is intended to include all modifications within the meanings and scopes equivalent to those of the claims.

Figure 8:
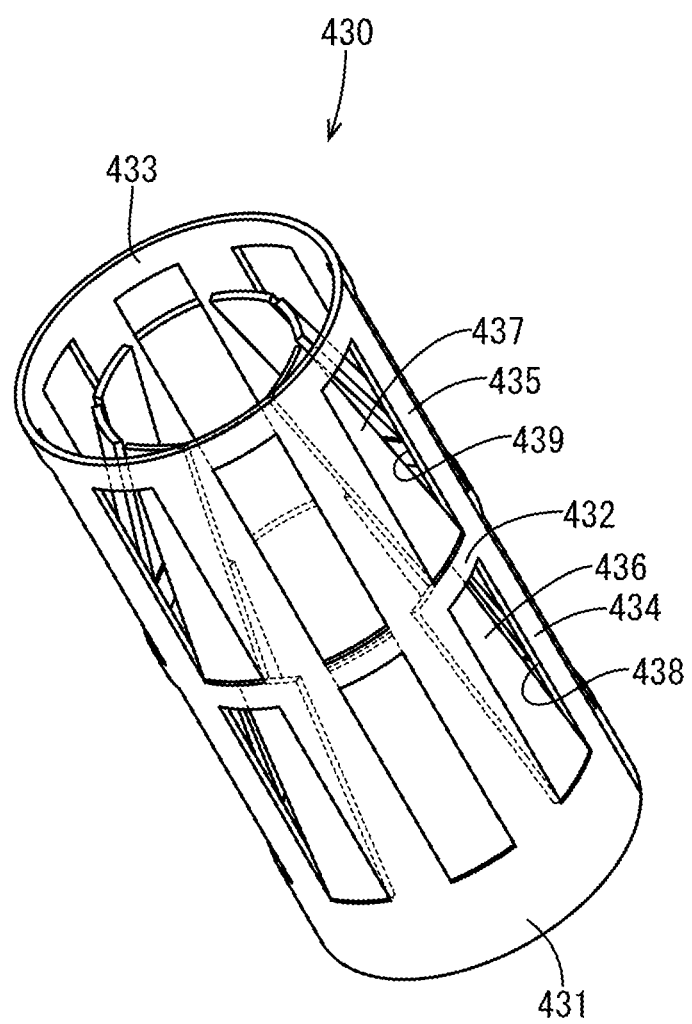
FIG. 8 is a perspective view of a heat dissipating outer tube according to a fourth embodiment of the present disclosure.
Figure 9:
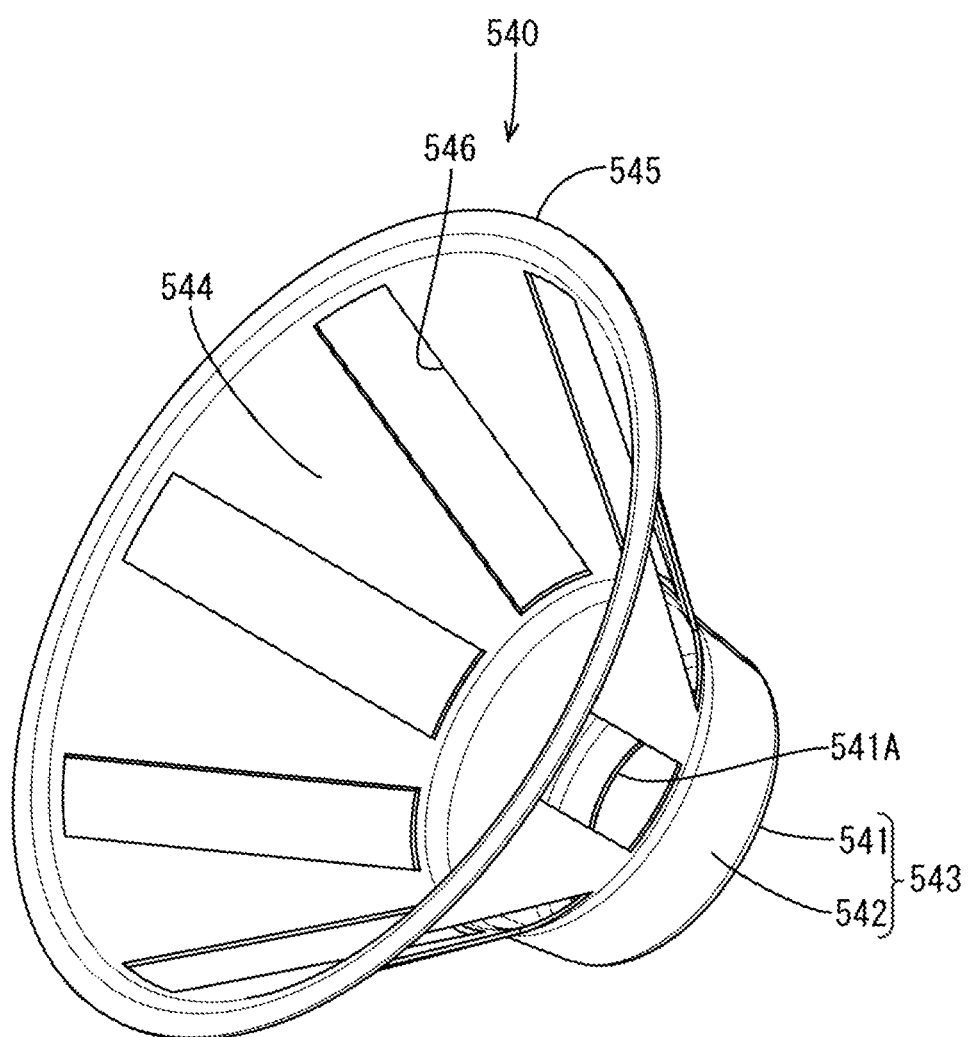
FIG. 9 is a perspective view of a heat blocking cover according to the fourth embodiment of the present disclosure.

The heat dissipating outer tube 430 of the fourth embodiment of the present disclosure has a shape different from the shape of the heat dissipating outer tube 330 of the third embodiment. The heat dissipating outer tube 430 has a cylindrical shape and opens toward the forward end side and the rear end side. As shown in FIG. 8, the heat dissipating outer tube 430 includes a connection portion 431 located on the forward end side and having a cylindrical shape, a second joining portion 433 located on the rear end side and having a cylindrical shape, a first joining portion 432 located between the connection portion 431 and the second joining portion 433 and having a cylindrical shape, a first main portion 434 connecting the connection portion 431 and the first joining portion 432, and a second main portion 435 connecting the first joining portion 432 and the second joining portion 433.

The first main portion 434 has a plurality of first flexible pieces 436 arranged in the circumferential direction. The first flexible pieces 436 are formed through cutting and bending so as to extend rearward while inclining toward the radially inner side. The holes formed as a result of the cutting and bending will be referred to as first heat dissipating openings 438. The first heat dissipating openings 438 are provided in a region including a part of the heat dissipating outer tube 430 located forward of the center of the heat dissipating outer tube 430 in the direction of the axial line AX.

The second main portion 435 includes a plurality of second flexible pieces 437 arranged in the circumferential direction. The second flexible pieces 437 are formed through cutting and bending so as to extend rearward while inclining toward the radially inner side. The holes formed as a result of the cutting and bending will be referred to as second heat dissipating openings 439. The second heat dissipating openings 439 are provided in a region including a part of the heat dissipating outer tube 430 located rearward of the center of the heat dissipating outer tube 430 in the direction of the axial line AX.

In partial regions in the circumferential direction, the flexible pieces 436 and 437 are in contact with the outer tube 103. Since the plurality of flexible pieces 436 and 437 are disposed to surround the outer tube 103 and the heat dissipating outer tube 430 is disposed to extend along the axial line AX, the heat dissipating outer tube 430 is disposed coaxially with the outer tube 103, whereby the heat dissipating outer tube 430 is prevented from approaching the outer tube 103. Since the heat dissipating outer tube 430 protrudes from the connection portion 103A of the outer tube 103 in a cantilevered fashion, the heat dissipating outer tube 430 tends to incline toward the outer tube 103 so that the second joining portion 433 approaches the outer tube 103. Such inclination of the heat dissipating outer tube 430 can be effectively prevented by the flexible pieces 436 and 437.

[Details of a Fifth Embodiment of the Present Disclosure]

A specific example of a heat blocking cover 540 of a fifth embodiment of the present disclosure will now be described with reference to the drawings. Notably, the present disclosure is not limited to the example. The scope of the present disclosure is defined by the claims and is intended to include all modifications within the meanings and scopes equivalent to those of the claims.

The heat blocking cover 540 of the fifth embodiment of the present disclosure has heat dissipating openings 546 having a shape different from the shape of the heat dissipating openings 346 of the heat blocking cover 340 of the third embodiment. Since the remaining structure is the same as that of the blocking cover 340 of the third embodiment, its description will not be repeated. The same structural portions as those in the third embodiment are denoted by the same reference numerals as those in the third embodiment, and the structural portions corresponding to those in the third embodiment are denoted by reference numerals obtained by changing the hundred-place digits (which are 3) of the respective reference numerals used in the third embodiment to 5.

Each of the heat dissipating openings 546 of the fifth embodiment has the shape of a rectangle whose short sides are located at the rear end and the forward end, and has a constant width from the forward end side toward the rear end side. The heat dissipating openings 546, the number of which is three or more, are disposed at equal intervals in the circumferential direction. In the present embodiment, eight heat dissipating openings 546 are provided in the diameter increasing portion 544.

[Other Embodiments]

(1) In the first to third embodiments, the rear end of the heat dissipating member 104 is located forward of the rear end of the outer tube 103. However, the rear end of the heat dissipating member may be located rearward of the rear end of the outer tube. In this case, when a region where the main portion and the outer tube overlap each other is defined as an overlapping region, the main portion may have heat dissipating openings—for establishing communication between the gap S and the space on the outer circumferential side of the heat dissipating member—on the rear end side of the center of the overlapping region in the direction of the axial line AX.

(2) In the first to third embodiments, the thickness (cross-sectional area) of the heat dissipating member 104 or 204 is rendered larger than the thickness (cross-sectional area) of the outer tube 103, so that the heat transfer resistance per unit length of the heat dissipating member 104 or 204 (the degree of difficulty in transferring heat through the heat dissipating member 104 or 204) decreases. However, the heat transfer resistance of the heat dissipating member may be decreased by using, as the material of the heat dissipating member, a metal material having a higher thermal conductivity than the metal material used for the outer tube 103. Both the outer tube 103 and the heat dissipating member 104 or 204 of the first and second embodiments are formed of SUS304. However, for example, the outer tube 103 may be formed of SUS304, and the heat dissipating member may be formed of an aluminum alloy.

(3) In the first to third embodiments, the outer tube is exposed to the outside through the heat dissipating openings. However, it is unnecessary to expose the outer tube to the outside through the heat dissipating openings, and the heat dissipating openings may have other forms so long as the gap S communicates with the space on the outer circumferential side of the heat dissipating member.

(4) In the first to third embodiments, the forward end portion of the heat dissipating member 104, 204, or 304 is integrally fixed to the mounting portion 110D by laser welding. However, the forward end portion of the heat dissipating member may be fixed by any of other welding methods such as resistance welding.

(5) In the first to third embodiments, the forward end portion of the heat dissipating member 104, 204, or 304 and the forward end portion of the outer tube 103 are caused to overlap each other and are fixed. However, the forward end portion of the outer tube 103 may be disposed on the rear end side of the forward end portion of the heat dissipating member 104, 204, or 304, and the heat dissipating member 104, 204, or 304 may be fixed directly to the mounting portion 110D of the metallic shell 110.

(6) In the first to third embodiments, the heat dissipating openings are holes having an inverted triangular shape or a rectangular shape. However, the heat dissipating openings may be holes having a shape other than the inverted triangular shape and the rectangular shape.

(7) In the first and second embodiments, the heat dissipating member 104 or 204 is not in contact with the outer tube 103 on the rear end side of the mounting portion 110D. However, the heat dissipating member may be in contact with the outer tube in a partial circumferential region.

(8) In the first to third embodiments, the gas sensors 100 and 200 exemplified are full range air-fuel ratio sensors. However, the type of gas sensors 100 and 200 is not limited thereto, and the gas sensors 100 and 200 may be lambda sensors, NOx sensors, etc.

(9) In the third to fifth embodiments, the heat dissipating member 304 is composed of the heat dissipating outer tube 330 and the heat blocking cover 340. However, the heat dissipating member may be composed of only one of the heat dissipating outer tube 330 and the heat blocking cover 340.

DESCRIPTION OF REFERENCE NUMERALS

10: exhaust pipe
20: thread groove
100: gas sensor
101: inner protector 101C: introduction hole
102: outer protector 102C: introduction hole
103: outer tube (a part of tubular housing 130) 103A: connection portion (large diameter portion) 103B: separator housing portion (small diameter portion) 103C: lead wire housing portion 103D: sealing member holding portion 103E: opening 103F: step portion 103G: joining portion
104: heat dissipating member 104A: connection portion
104B: main portion
105: welded portion
106: heat dissipating opening
110: metallic shell (a part of tubular housing 130) 110A: threaded portion 110B: tool engagement portion 110C: protector connection portion
110D: mounting portion
111: ceramic holder
112: powder filled layer
113: ceramic sleeve
114: crimp ring
120: gas sensor element
121: gas detection portion
130: tubular housing (103, 110)
181: separator
182: sensor connection terminal
183: heater connection terminal
190: urging metal member
191: sealing member
193: sensor lead wire
194: heater lead wire
200: gas sensor
204: heat dissipating member 204A: connection portion 204B: main portion
206: heat dissipating opening
300: gas sensor
304: heat dissipating member
305: welded portion
330: heat dissipating outer tube 331: connection portion 332: main portion 333: joining portion 334: stationary piece 335: flexible piece 335A: straight portion 335B: inclined portion 336: heat dissipating opening
340: heat blocking cover 341: bottom wall portion 341A: insertion hole 342: tubular portion 343: connection portion 344: diameter increasing portion 345: flange portion 346: heat dissipating opening
430: heat dissipating outer tube 431: connection portion 432: first joining portion 433: second joining portion 434: first main portion 435: second main portion 436: first flexible piece 437: second flexible piece 438: first heat dissipating opening 439: second heat dissipating opening
540: heat blocking cover 541: bottom wall portion 541A: insertion hole 542: tubular portion 543: connection portion 544: diameter increasing portion 545: flange portion 546: heat dissipating opening
AX: axial line
H1: through hole H2: through hole H3: through hole H4: through hole
S: gap

The invention claimed is:

1. A gas sensor extending in an axial direction from a forward end toward a rear end, the gas sensor comprising:
a gas sensor element that is configured to detect a concentration of a specific gas in a gas under measurement;
a tubular housing surrounding the gas sensor element and having an opening at a rear end thereof;
a sealing member closing the opening; and
a tubular heat dissipating member surrounding the housing and having a rear end located at the same position as the rear end of the housing or located forward of the rear end of the housing, the heat dissipating member reducing the amount of heat transferred from a forward end side of the gas sensor to the sealing member through the housing, wherein
the heat dissipating member includes a connection portion connected to the housing on a forward end side of the sealing member, and a main portion extending rearward from the connection portion such that a gap is formed between the main portion and the housing, and the main portion has a heat dissipating opening that is configured to establish communication between the gap and a space on an outer circumferential side of the heat dissipating member, the heat dissipating opening being located rearward with respect to a center of the main portion in the axial direction.

2. A gas sensor extending in an axial direction from a forward end toward a rear end, the gas sensor comprising:
a gas sensor element that is configured to detect the concentration of a specific gas in a gas under measurement;
a tubular housing surrounding the gas sensor element and having an opening at a rear end thereof;
a sealing member closing the opening; and
a tubular heat dissipating member surrounding the housing and having a rear end located rearward of the rear end of the housing, the heat dissipating member reducing the amount of heat transferred from a forward end side of the gas sensor to the sealing member through the housing, wherein
the heat dissipating member includes a connection portion connected to the housing on a forward end side of the sealing member, and a main portion extending rearward from the connection portion such that a gap is formed between the main portion and the housing,
the main portion has a heat dissipating opening that is configured to establish communication between the gap and a space on an outer circumferential side of the heat dissipating member, and
the heat dissipating opening is located rearward in the axial direction with respect to a center of a region where the main portion and the housing overlap each other in the axial direction.

3. The gas sensor according to claim 1, wherein a length of the heat dissipating opening in the axial direction is greater than a half of a length of the heat dissipating member in the axial direction.

4. The gas sensor according to claim 1, wherein the heat dissipating opening gradually increases in width from the forward end side toward the rear end side.

5. The gas sensor according to claim 1, wherein the length of the heat dissipating opening in the axial direction is greater than a length of the heat dissipating opening in a direction perpendicular to the axial direction.

6. The gas sensor according to claim 1, wherein the housing includes:
a metallic shell surrounding the gas sensor element and having a tool engagement portion and a mounting portion disposed on the rear end side of the tool engagement portion to be continuous with the tool engagement portion; and
an outer tube extends rearward from the metallic shell, surrounding the gas sensor element, and including a large diameter portion having a welded portion welded to the mounting portion together with the connection portion, a small diameter portion located rearward of the large diameter portion and being smaller in diameter than the large diameter portion, and a joining portion joining a rear end of the large diameter portion and a forward end of the small diameter portion, wherein
a forward end of the heat dissipating opening is located rearward with respect to the welded portion and is located forward with respect to the joining portion.

7. The gas sensor according to claim 1, wherein, when the heat dissipating opening is viewed in a cross-sectional plane perpendicular to the axial direction,
a portion of the heat dissipating member on an outer side in a thickness direction thereof has a shape such that a distance between that portion and the widthwise center of the heat dissipating opening gradually decreases toward an inner side in the thickness direction, and
a portion of the heat dissipating member on the inner side in the thickness direction has a shape that protrudes toward the inner side in the thickness direction.

8. The gas sensor according to claim 1, wherein the heat dissipating member has three or more heat dissipating openings formed such that the heat dissipating openings are arranged in a circumferential direction at equal intervals.

9. The gas sensor according to claim 1, wherein the heat dissipating member has an inward projecting portion projecting toward a radially inner side, and the inward projecting portion is in contact with the housing in a partial circumferential region.

* * * * *